(12) United States Patent
Martin

(10) Patent No.: US 8,757,828 B2
(45) Date of Patent: Jun. 24, 2014

(54) DRIP CHAMBER ILLUMINATION DEVICE

(76) Inventor: Coleman Martin, Leawood, KS (US)

( * ) Notice: Subject to any disclaimer, the term of this patent is extended or adjusted under 35 U.S.C. 154(b) by 5 days.

(21) Appl. No.: 13/605,251

(22) Filed: Sep. 6, 2012

(65) Prior Publication Data

US 2014/0063780 A1    Mar. 6, 2014

(51) Int. Cl.
*F21V 33/00* (2006.01)
*F21V 9/00* (2006.01)
*F21S 8/00* (2006.01)

(52) U.S. Cl.
USPC ............ 362/96; 362/109; 362/231; 362/431; 362/572; 362/800; 362/804

(58) Field of Classification Search
None
See application file for complete search history.

(56) References Cited

U.S. PATENT DOCUMENTS

| | | | |
|---|---|---|---|
| 3,217,709 A | 11/1965 | Schneider et al. | |
| 5,690,612 A * | 11/1997 | Lopez et al. | 604/95.05 |
| 5,695,466 A | 12/1997 | Lopez et al. | |
| 5,843,045 A | 12/1998 | DuPont | |
| 6,050,713 A | 4/2000 | O'Donnell et al. | |
| 6,159,186 A | 12/2000 | Wickham et al. | |
| 6,877,877 B2 * | 4/2005 | Rodriguez et al. | 362/231 |
| 6,984,052 B1 | 1/2006 | Del Castillo | |
| 7,052,158 B2 | 5/2006 | Rodriquez et al. | |
| 7,351,231 B2 | 4/2008 | Young | |
| 2004/0160770 A1 * | 8/2004 | Rodriguez et al. | 362/234 |
| 2005/0117335 A1 * | 6/2005 | Rodriquez et al. | 362/231 |
| 2006/0291211 A1 * | 12/2006 | Rodriguez et al. | 362/249 |

FOREIGN PATENT DOCUMENTS

| | | |
|---|---|---|
| EP | 0491971 A1 | 7/1992 |
| WO | 2007117656 A2 | 10/2007 |

* cited by examiner

*Primary Examiner* — Natalie Walford
(74) *Attorney, Agent, or Firm* — Husch Blackwell LLP

(57) ABSTRACT

A drip chamber illumination device including a body and an illumination arm coupled to the body. A light source is disposed on or near the end of the illumination arm wherein the light source may comprise at least one light, but preferably two lights spatially offset that are directed toward a substantially common focal area. The lights may be able to illuminate in different colors. The illumination device further includes a clip attached to the body and configured to removably couple the illumination device to a tube/flush line positioned below a drip chamber. A switch on the device allows a user to selectively provide power from a power source to the lights. The illumination arm may be angled with respect to the body so that the illumination arm may have a substantially vertical orientation when and embodiment of the illumination device is clipped to the tube.

20 Claims, 7 Drawing Sheets

DRIP CHAMBER ILLUMINATION DEVICE

CROSS-REFERENCE TO RELATED APPLICATIONS

None.

BACKGROUND OF THE INVENTION

This invention relates to an apparatus used during the medical infusion of fluids. Fluids are generally supplied to a patient during an operation or a minimally invasive procedure under the force of gravity by positioning a container containing the fluid at an elevated position relative to, the patient or, in the setting of arteriography, supplied with the aid of a pressure bag to ensure delivery fluid (also known as "flush") against a significant pressure gradient. The rate of flow is set by a manually adjustable clamp positioned in the line between the bag and the patient. The fluid flows from the fluid bag to the patient via a drip chamber attached to the lower or outlet end of the fluid bag. The drip chamber includes a drop former which operates to generate discrete, successive drops which fall from the drip former into a reservoir defined at the lower end of the drip chamber from which the fluid flows to the patient via tubing. The drip chamber is transparent so that the drips may be observed by members of the health care team to insure that drippage is occurring and to further insure that the drippage rate is within appropriate, predetermined limits.

Some minimally invasive surgical procedures require a darkened operating room environment, particularly those wherein the surgeon visualizes the operation by an endoscope, a video, or an X-ray imaging monitor. When a procedure or treatment occurs in a darkened environment, it makes monitoring the drip chamber difficult. Because the surgeon or anesthesiologist must divide his or her attention between multiple technical and patient factors, the drippage flow must be readily visible from multiple angles to allow all members of the health care team to monitor drippage.

It is especially critical that a proper drippage rate be maintained and verified during trans-arterial neurointerventional procedures. These procedures require frequent adjustments of the drippage rate to balance the pressure gradient determining flow rate which itself depends on three fluctuating variables, the patient's blood pressure, the resistance within the catheter system, and the delivery pressure imposed by the pressure bag (which falls as the quantity of flush within the fluid bag is depleted). If the drippage rate is not closely monitored and adjusted during neurointerventional procedures, the loss of drippage flow during these procedures may allow arterial blood to enter a catheter, clot and embolize to a cerebral blood vessel resulting in a stroke which could be fatal to the patient.

There is therefore a need in the art for an illumination device which allows the drip chamber to be viewed from substantially any angle so that it can be monitored from various positions in the operating or treatment room.

Further, bubbles may be unintentionally introduced to the drip chamber reservoir with high rates of drippage flow, improper filling of the reservoir with either too much or too little volume, or with emptying of the fluid bag. The presence of bubbles within the reservoir poses a significant hazard to the patient undergoing neurointerventional procedures. Bubbles circulating in the drip chamber reservoir which are allowed to pass from the reservoir to the tubing typically pass through the catheter and into a brain artery and may result in a cerebral air embolism and stroke. This occurrence may also be fatal to the patient. Because bubbles in the drip chamber reservoir are typically in the millimeter range, such bubbles are difficult to identify even with normal ambient lighting.

There is therefore a need in the art for an illumination device configured to illuiminate the drip chamber reservoir in order to maximize the appearance of any bubbles that may have formed in the reservoir.

Neurointerventional procedures are often performed with multiple (in some cases as many as seven) arterial and/or venous flush lines making identification of which drip chamber is associated with which catheter difficult. Colored stickers affixed to the flush chambers aid identification, however, these stickers partially obscure the drip chamber and visualization of these stickers is difficult with low ambient light.

There is therefore a need in the art to provide an illumination device which may emit light of various colors in order to differentiate the drip chambers of multiple arterial and/or venous flush lines by color.

This application outlines a device which provides a novel, non-obvious solution to both the illumination and identification problems associated with visually monitoring drippage flow.

SUMMARY OF THE INVENTION

The present invention is directed toward a drip chamber illumination device in which the drippage condition of the fluid may be verified from substantially any angle with minimal light contamination of the operating room conditions. The drip chamber illumination device may include light sources which, from below and at acute angles, illuminate a drip chamber to allow visual identification that the fluid is being administered at the desired flow rate. The illumination device comprises a body and an illumination arm coupled to or integral with the body portion. The illumination arm may be at an angular orientation with respect to the body. The angular orientation of the illumination arm may allow it to be orientated in a substantially upright position when the present illumination device is clipped to the tube/flush line, particularly in an embodiment wherein the center of mass is a distance from the connection point. In such a case, the device rotates under its own weight to an equilibrium position where the center of mass is substantially below the connection point and the angular orientation of the arm compensates for the rotation to place the illumination arm in a substantially vertical orientation after the rotation.

The illumination arm may include at least one light. Another embodiment may include two or more lights. The lights of the illumination arm may be spatially offset and aimed at an acute angle and/or at a substantially common focal area. The illumination arm may include at least two arms wherein each arm includes at least one light. The lights may be either mono or polychromatic light emitting diodes ("LED"). One embodiment may include polychromatic LEDs which allow each illumination device to be set to a different color when multiple drip chambers are being used during a procedure. The polychromatic LEDs help medical personnel differentiate the fluid being administered by color. The light color may be selected using a dial switch or other mechanism, or color selection may be integrated into the power switch or other known control device.

The present illumination device further includes a clip allowing a user to clip the illumination device onto a tube/flush line located below the drip chamber. The clip may include a spring or biasing member to apply a clamping force on the tubing between an end of the clip and either the body or the illumination arm. The clip, the body, and/or the illumination arm may have a notch disposed thereon configured to engage the tube/flush line. The notches may be configured to center the illumination device on the tubing.

The present illumination device may also be turned on by operating a switch disposed on the body to selectively operate a power source. The power source may be batteries positioned within the body, a cable to attach multiple illumination devices to a common power supply, or any other known power source.

Other aspects and advantages of the present invention will be apparent from the following detailed description of the preferred embodiments and the accompanying drawing figures.

BRIEF DESCRIPTION OF THE SEVERAL VIEWS OF THE DRAWING

The accompanying drawings form a part of the specification and are to be read in conjunction therewith, in which like reference numerals are employed to indicate like or similar parts in the various views.

DETAILED DESCRIPTION OF THE INVENTION

The following detailed description of the present invention references the accompanying drawing figures that illustrate specific embodiments in which the invention can be practiced. The embodiments are intended to describe aspects of the present invention in sufficient detail to enable those skilled in the art to practice the invention. Other embodiments can be utilized and changes can be made without departing from the spirit and scope of the present invention. The present invention is defined by the appended claims and, therefore, the description is not to be taken in a limiting sense and shall not limit the scope of equivalents to which such claims are entitled.

Figure 1:
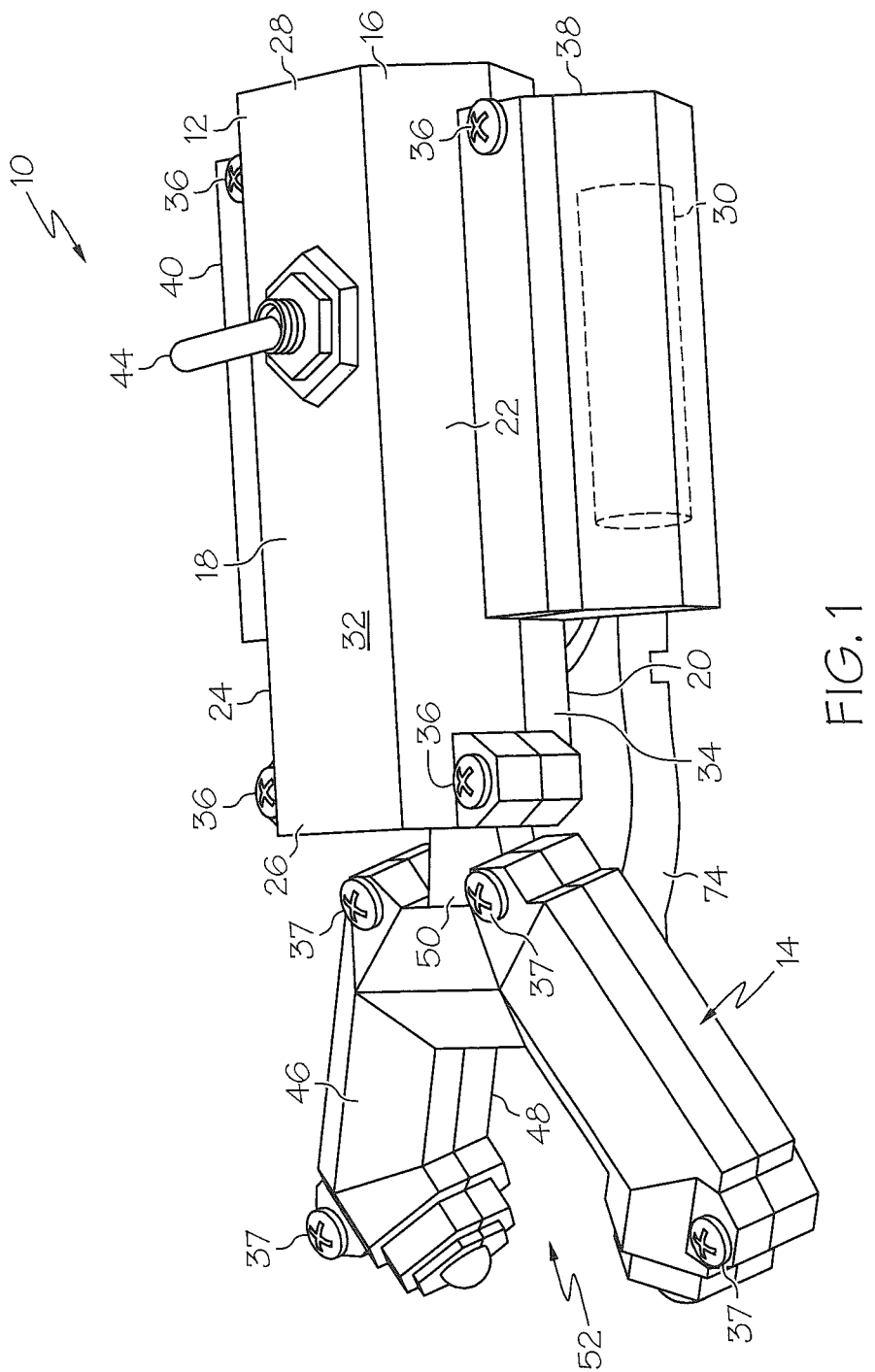
FIG. 1 is a perspective view of one embodiment of the present illumination device constructed in accordance with the teachings of the present invention.
Figure 3:
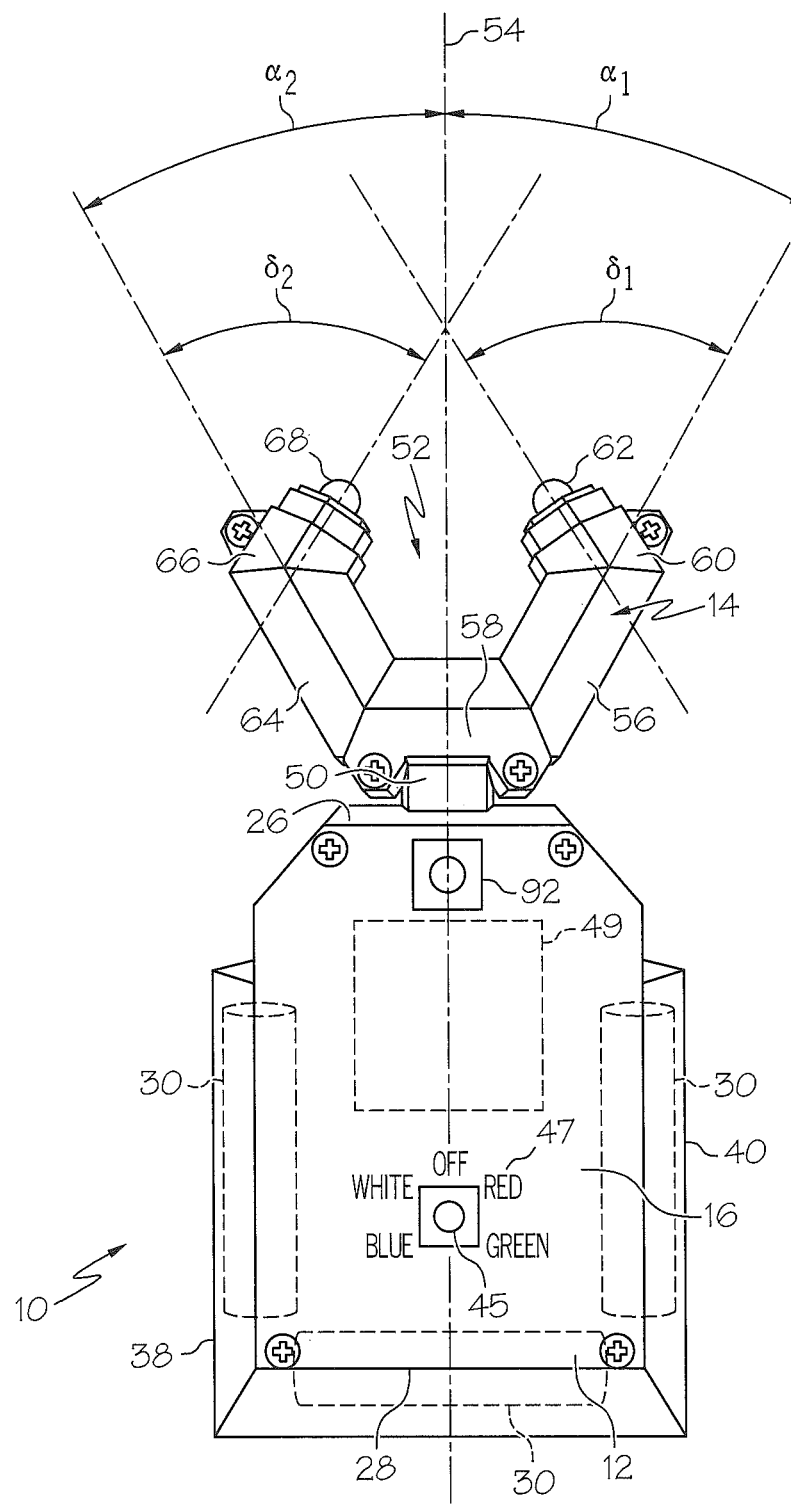
FIG. 3 is a top plan view of one embodiment of the present illumination device constructed in accordance with the teachings of the present invention.

As illustrated in FIG. 1, the present invention is directed toward a drip chamber illumination device 10 configured to illuminate a drip chamber in a darkened operating or other patient treatment room wherein low light or dark room conditions exist. Illumination device 10 includes a body 12 and an illumination arm 14 coupled to body 12. Body 12 includes a body housing 16 which includes a front 18, a back 20, a first side 22, a second side 24, a first end 26 and a second end 28. Body housing 16 may include one or more hollow sections that house a power source 30. As shown in FIG. 3, one embodiment of the present illumination device 10 includes body 12 housing three batteries 30. Power source 30 may include any number of batteries necessary for operative use of the device 10 and may include batteries of any type now known or hereafter developed including alkaline, ni-cad, lithium, single-use or rechargeable in any size or voltage required to meet the power requirements of illumination device 10. Alternatively, body housing 16 may house circuitry which provides illumination device 10 the ability to be operated by being connected by a wire to an alternating current power source such as a conventional plug for engagement with a conventional power outlet, a direct current common battery source for one or more illumination devices 10, or any other power source now known or hereafter developed. An embodiment of illumination device 10 (not shown) may be hard-wired to a connector that connects to the external power source and includes either a wire or cord extending from body 12 or a removable power cord. In a preferred embodiment, power source 30 is not a conventional power distribution level alternating current power source in order to eliminate any risk of a shock hazard to a patient in a potentially wet operating or recovery room environment.

Figure 2:
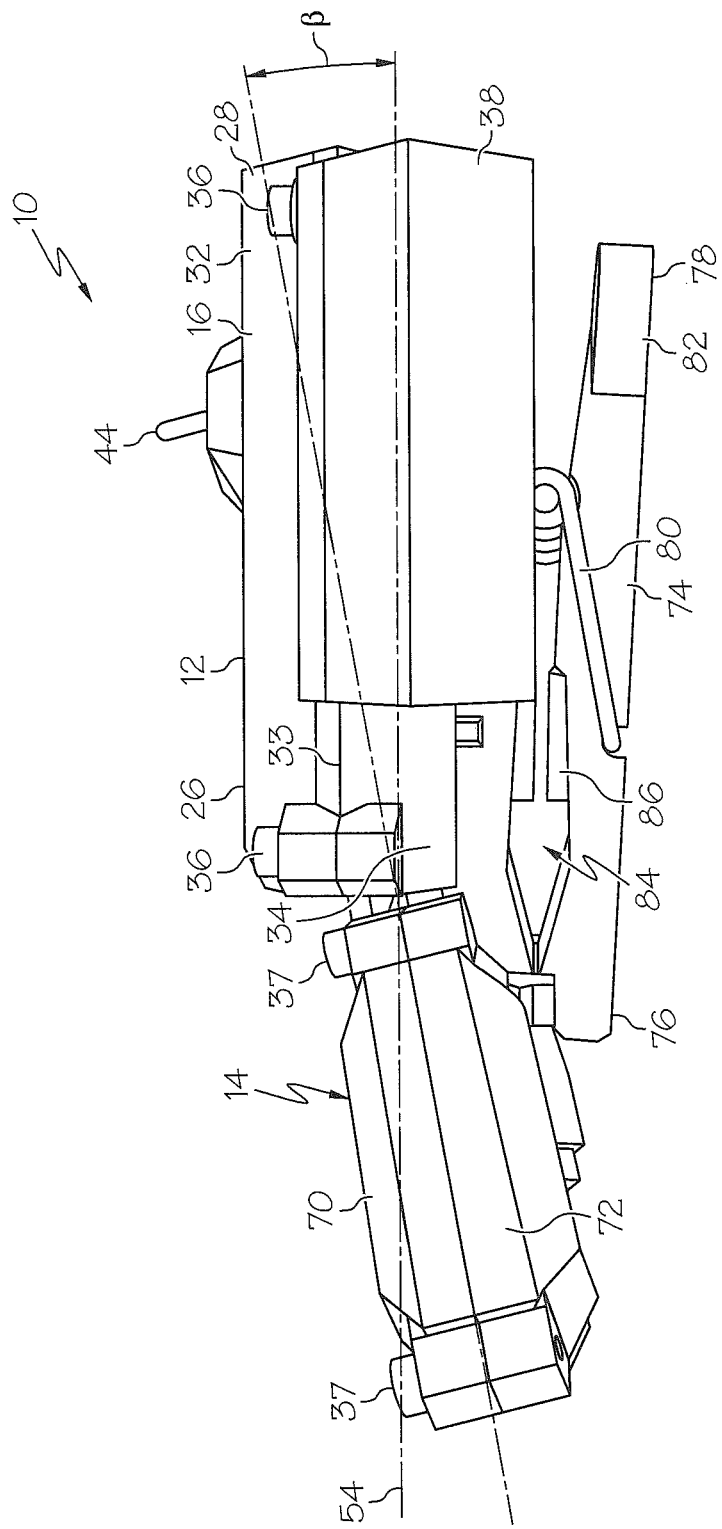
FIG. 2 is a side elevational view of one embodiment of the illumination device of FIG. 1.

As best shown in FIG. 2, one embodiment of illumination device includes body housing 16 having a front half portion 32 and a back half portion 34 which are coupled together with fasteners 36 forming joint 33 as shown. In another embodiment, power source 30 is inserted into a cavity in either the front half portion 32 or the back half portion 34 and the two half portions 32 and 34 are aligned and coupled together by fasteners 36. Fasteners 36 may be screws, rivets, adhesive, bolts, snap closure, spring loaded tabs, or any other fastener now known or hereafter developed. Body housing 16 may also include one or more battery compartments 38 and 40 which are configured to receive batteries. As shown in FIG. 3, battery compartments 38 and 40 may be located proximate the second end 28 of body 12. The position and mass of any batteries within housing 16 contributes to the center of mass 42 of illumination device 10. Body 12 may also include a switch 44 which allows a user to selectively operate the power source 30.

Body 12 may be constructed from any material now known or hereafter developed including molded, extruded, or machined polymers, cast, formed, or machined metals, or any combination thereof. Body 12 may further be constructed using any other forming technique or material now known or hereafter developed. In one embodiment, body 12 may include two pieces of thermoplastic coupled together as shown in FIG. 1. In another embodiment, body 12 may be stainless steel which may be easily sterilized for operating room use.

Illumination arm 14 may be coupled to or formed integral with body 12 as shown in FIG. 1. Illumination arm 14 includes an arm front 46, an arm back 48, a body end 50 and an illumination end 52. However, embodiment of illumination arm 14 (not shown) may alternatively be one arm extending away from body 12. One embodiment shown in FIG. 2 includes the illumination arm 14 being coupled to body 12 in an angular orientation resulting in a bend in the illumination device 10 as shown. More particularly, FIG. 2 illustrates an embodiment wherein illumination arm 14 is coupled to body 12 at an angle $\beta$ with respect to a longitudinal axis 54 of body 12. However, illumination arm 14 may be coupled to body 12 substantially parallel to longitudinal axis 54 and be substantially linear.

As shown in FIG. 3, illumination arm 14 includes a first arm 56 which branches off of a trunk 58 and extends outwardly away from trunk 58 and body 12. First arm 56 extends at an angle $\alpha_1$ from a longitudinal axis 54 of body 12. One embodiment of illumination arm 14 includes first arm 56 being integral with trunk 58. An alternative embodiment includes first arm 56 being pivotally coupled to trunk 58 wherein first arm 56 may be coupled to truck 58 with a fastener 37. Fastener 37 may be configured to be loosened to allow for rotating first arm 56 with respect to trunk 58 and tightened to secure the position of first arm 56.

First arm 56 may further include first return portion 60 that is orientated at an angle $\delta_1$ relative to arm 56. One embodiment of illumination arm 14 includes first return portion 60 being integral with arm 56. An alternative embodiment includes first return portion 60 being pivotally coupled to arm 56 wherein first return portion 60 may be coupled to arm 56 with a fastener 37. Fastener 37 may be configured to be loosened to allow for rotating first return portion 60 with respect to first arm 56 and tightened to secure the position of first return portion 60. A first light 62 may be disposed on first arm 56 and may be aimed inwardly toward the longitudinal axis 54 of body 12.

Further, the embodiment of illumination arm 14 illustrated in FIG. 3 also includes at least a second arm 64 which also branches off trunk 58 and extends outwardly at an angle $\alpha_2$ from the longitudinal axis 54 as shown. Similarly, second arm 64 may likewise include a second return portion 66 orientated at an angle $\delta_2$ relative to second arm 64. Second arm 64 and second return portion 66 may similarly be configured as fixed or adjustable through a pivot connection that may be adjusted by tightening and loosening screw 37. A second light 68 is disposed upon the second arm 64 and may be aimed inwardly toward the longitudinal axis 54 of body 12.

One embodiment includes lights 62 and 68 being disposed upon a terminal end of return portions 60 and 66, respectively, and aimed toward a substantially common focal area. In another embodiment, arms 56 and 64 do not include return portions 60 and 66 and the lights 62 and 68 can be disposed on arms 56 and 64 and similarly aimed inwardly toward a common focal area. Yet another embodiment includes only the first light 62 disposed on illumination arm 14 such that it is aimed upward and inwardly toward the longitudinal axis 54 of body 12.

Lights 62 and 68 may be any light now known or hereafter developed. A preferred embodiment includes light 62 and/or 68 being polychromatic light-emitting diodes (LED) which have the capability to vary the color (such as red, green, blue, white or any other color within the visible spectrum) of the light emitted. Further, illumination device 10 may be configured such that a user may use switch 44 as shown in FIG. 1, a momentary or other push-button switch 45 as shown in FIG. 3, or a dial switch (not shown) to vary the color of the lights. As further shown in FIG. 3, push-button switch 45 may be selectively depressed to change the color of the light to be emitted. In another embodiment, switch 44 or a dial switch may be selectively moveable to color indicators 47 disposed on body 12 to indicate the color of the light to be emitted. Switch 44 or push-button switch 45, or a dial switch may be in electronic communication with circuitry known in the art configured to illuminate a light of different color in response to changes in the position of switch 44, push-button switch 45, or a dial switch. As shown in FIG. 3, circuit board 49 is housed within housing 16 and is operably connected to power source 30 and switch 44, push-button switch 45, or a dial switch. A single color LED is also within the scope of the illumination device 10 of the present invention. In this embodiment, switch 44, push-button switch 45, or a dial switch would be an "on" and "off" switch.

Lights 62 and 68 may be a fluorescent, halogen, incandescent, light emitting diode, compact fluorescent, fiber optic, any combination thereof, or any other luminary now known or hereafter developed. Another embodiment of illumination device 10 includes lights 62 or 68 being low current, high efficiency, ultra-bright LED illuminators which do not require much power and provide increased energy efficiency. An embodiment of the present illumination device 10 which includes energy efficient LED illuminators and certain rechargeable batteries within body housing 16 may be configured such that the present illumination device 10 may be used for about a week on a single charge. Another embodiment of illumination device 10 (not shown) may be cabled to a common battery supply with sufficient battery capacity to provide power to multiple illumination devices and configured to last up to about two months on a set of batteries.

Illumination arm 14 and components thereof may be made from any material now known or hereafter developed including molded, extruded, or machined plastic or other polymers, cast, formed, or machined metals, or any combination thereof. Illumination arm 14 may further be constructed using any other forming or machining technique and material now known or hereafter developed. In one embodiment, illumination arm 14 may be combined into two pieces, arm front portion 70 and arm back portion 72 as shown in FIG. 2 wherein these pieces may be coupled to each other and then coupled to body 12 in either a fixed or pivoting manner. In another embodiment, body 12 and illumination arm 14 may be made of stainless steel which may be easily sterilized for operating room use. As shown in FIGS. 1 and 2, another embodiment of illumination device 10 includes body 12 and illumination arm 14 being integrally formed into a single front portion and a single back portion wherein the two pieces are coupled using fasteners 36 and 37.

Figure 4:
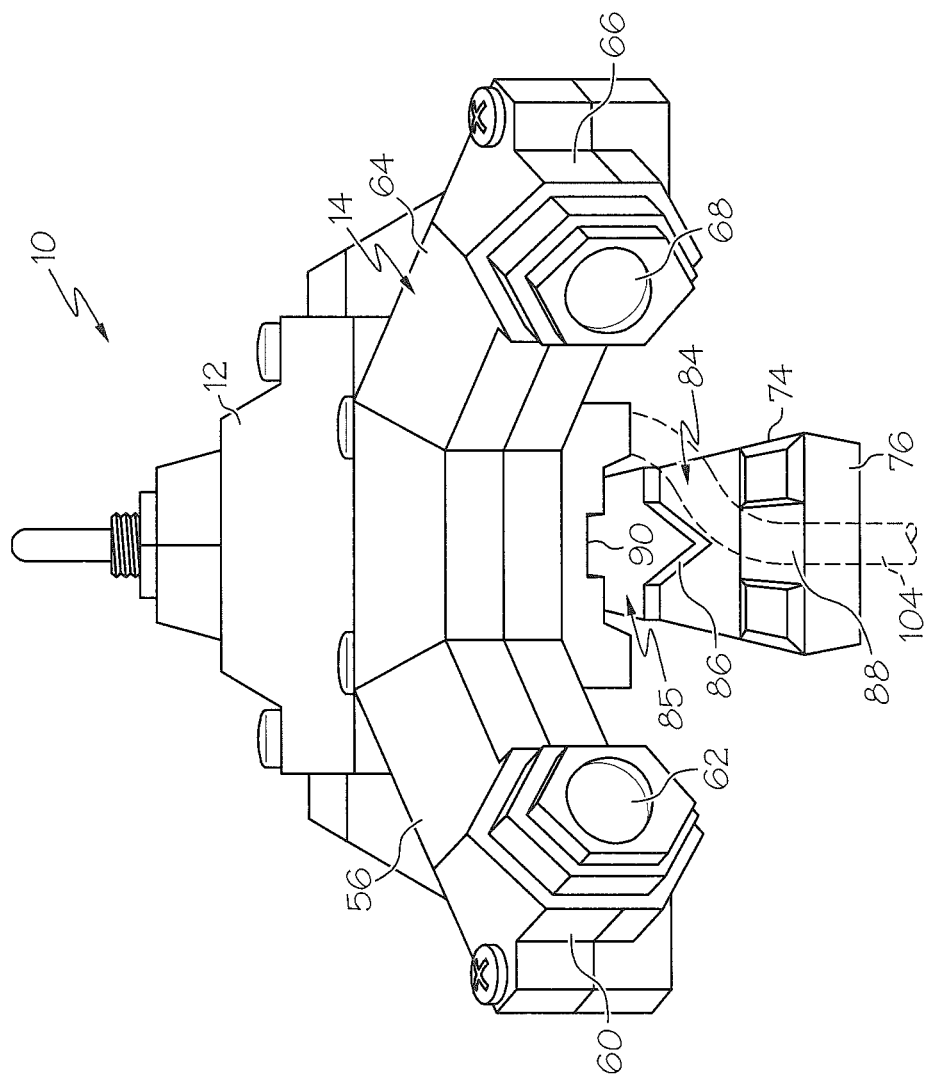
FIG. 4 is a front elevational view of one embodiment of the illumination device of FIG. 1.

Illumination device 10 further includes a clip 74 operably connected to body 12. As shown in FIG. 2, clip 74 is operably connected to back 20 of body 12. Clip 74 has a first end 76, a second end 78 and a spring or other biasing means 80 which may attach clip 74 to body 12 and may effectuate a clamping force upon clip 74 such that first end 76 bears against back 20 of body 12. Spring 80 may also be the fulcrum of clip 74 as shown in FIG. 2. Alternatively, clip 74 may be otherwise pivotally coupled to back 20 of body 12 and spring 80 may only exert the clamping force. Clip 74 may function similarly to a conventional clothes pin wherein clip 74 is a moveable half of a conventional clothes pin and the body 12 acts as a stationary half. Clip 74 may also include a thumb rest portion 82 proximate the second end 78. A user may apply a force toward back 20 using their thumb or finger applied to thumb rest portion 82 of second end 78 wherein the force applied to second end 78 overcomes the resistive force of spring or biasing member 80 thereby causing translation of first end 76 outwardly from back 20. As shown in FIG. 4, first end 76 may be displaced outwardly resulting in a space 85 between first end 76 of clip 74 and back 20 such that the tube/flush line 104 positioned below a drip chamber may be inserted therebetween. Once the force on second end 78 is released, the clamping force of spring 80 then closes first end 76 against back 20 thereby clamping the tube/flush line 104 between the two. The clamping force applied by spring 80 should be sufficient to secure illumination device 10 to the tube/flush line 104, but not enough to pinch the tube/flush line and interfere with the flow of the fluid into the patient.

As shown in FIGS. 2 and 4, one embodiment of clip 74 is configured to provide a gap 84 between clip 74 and back 20 to allow space for the tube/flush line 104 positioned below a drip chamber to pass through clip 74 without being impeded or having the fluid flow restricted. To assist in guiding the tube/flush line through clip 74, clip 74 may also include a guide wedge 86 that directs the tube/flush line through gap 84. Guide wedge 86 may also help prevent the tube/flush line from bunching up in clip 74 and may also keep it in a linear path so as to ensure unimpeded fluid flow through the tube.

As shown in FIG. 4, clip 74 may also be self-aligning and include a self-aligning clip notch 88 in first end 76. Back 20 of body 12 or back 48 of illumination arm 14 may also include a self-aligning notch 90 that is complimentary and aligned with self-aligning clip notch 88. Notches 88 and 90 may be configured to receive all or a portion of the cross-section of the tube/flush line 104 below a drip chamber so that (1) illumination device 10 remains centered on the tube/flush line to ensure the light is focused on the drip chamber, (2) illumination device 10 does not get bumped laterally or moved sideways during a surgical or treatment procedure, and (3) the clamping force applied to the tube/flush line at first end 76 is distributed around the perimeter of the tube/flush line so that clip 74 does not pinch and restrict fluid flow therethrough.

Clip 74 and spring 80 may be made of any material now known or hereafter developed including molded, extruded, or machined polymers, cast, formed, or machined metals, or any combination thereof. Clip 74 and spring 80 may further be constructed using any other forming technique or material now known or hereafter developed.

Figure 5:
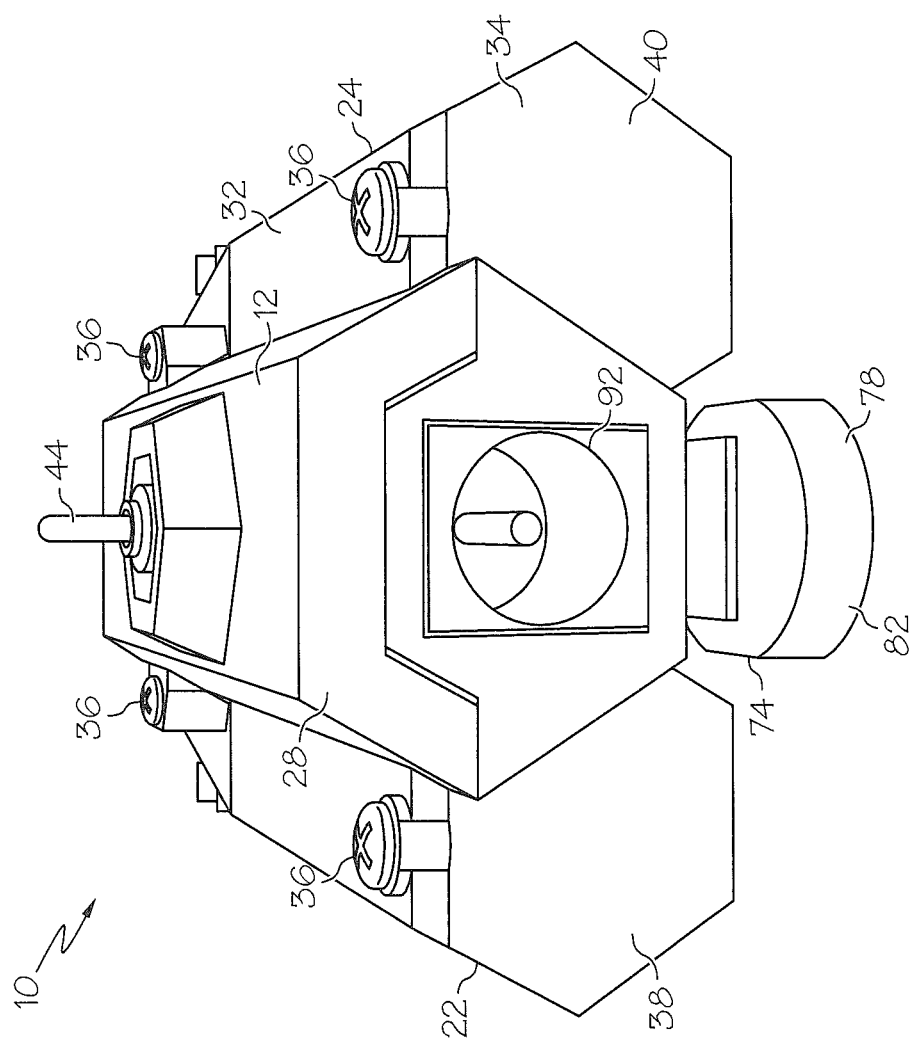
FIG. 5 is a rear elevational view of one embodiment of the of the illumination device of FIG. 1.

FIG. 5 illustrates a view of second end 28 of body 12 including a socket 92 configured to receive an A/C or D/C power supply cord. Alternatively, socket 92 may be configured to receive a plug to recharge any batteries housed within housing 16 of body 12. Socket 92 may be located proximate second end 28 of body 12 as shown, or disposed anywhere on body 12 including the front 18, the back 20, the first side 22, the second side 24, or the first end 26.

Figure 6:
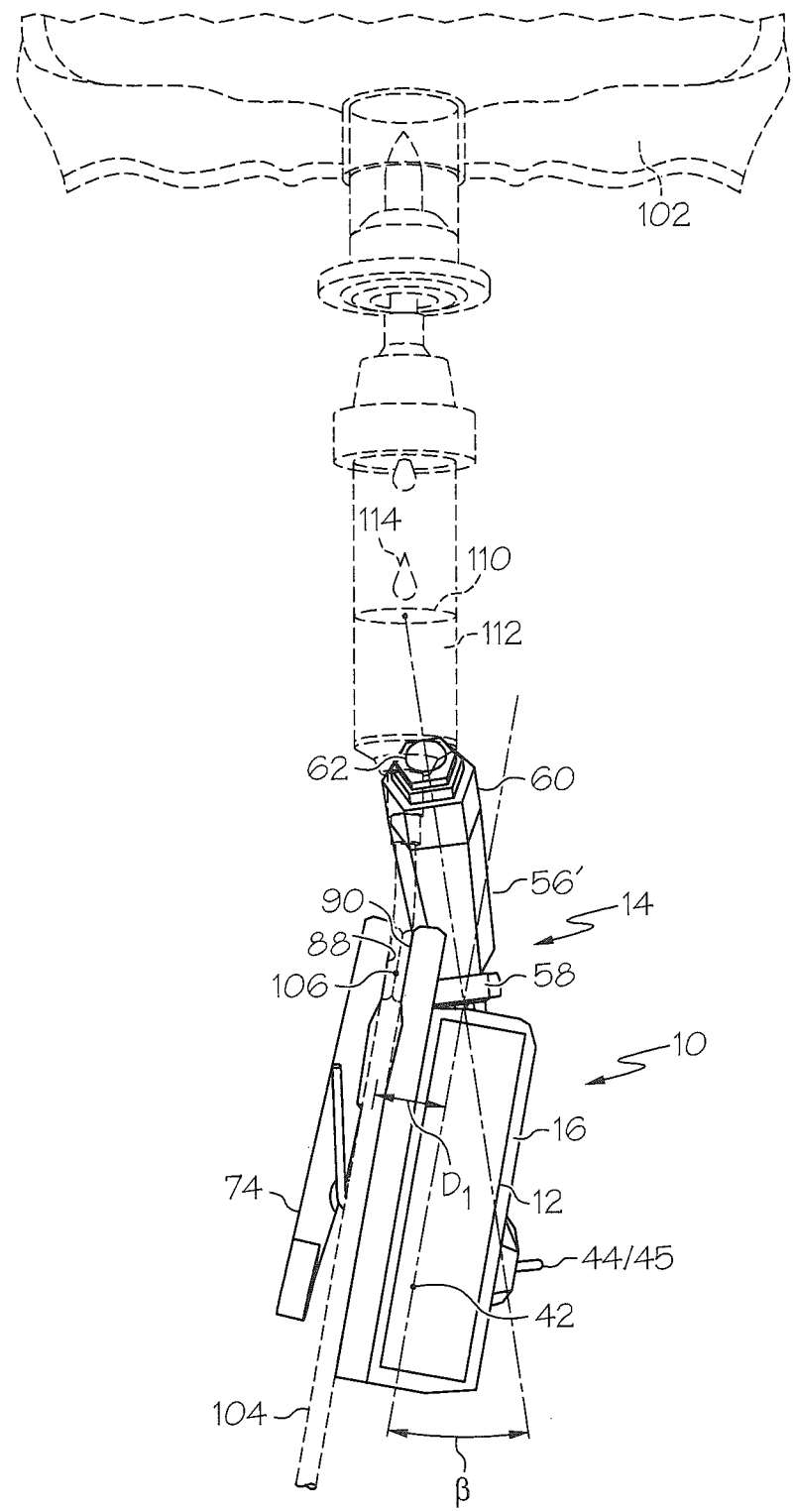
FIG. 6 is a side sectional view of the illumination device of FIG. 7 taken along the line 6-6 of FIG. 7.
Figure 7:
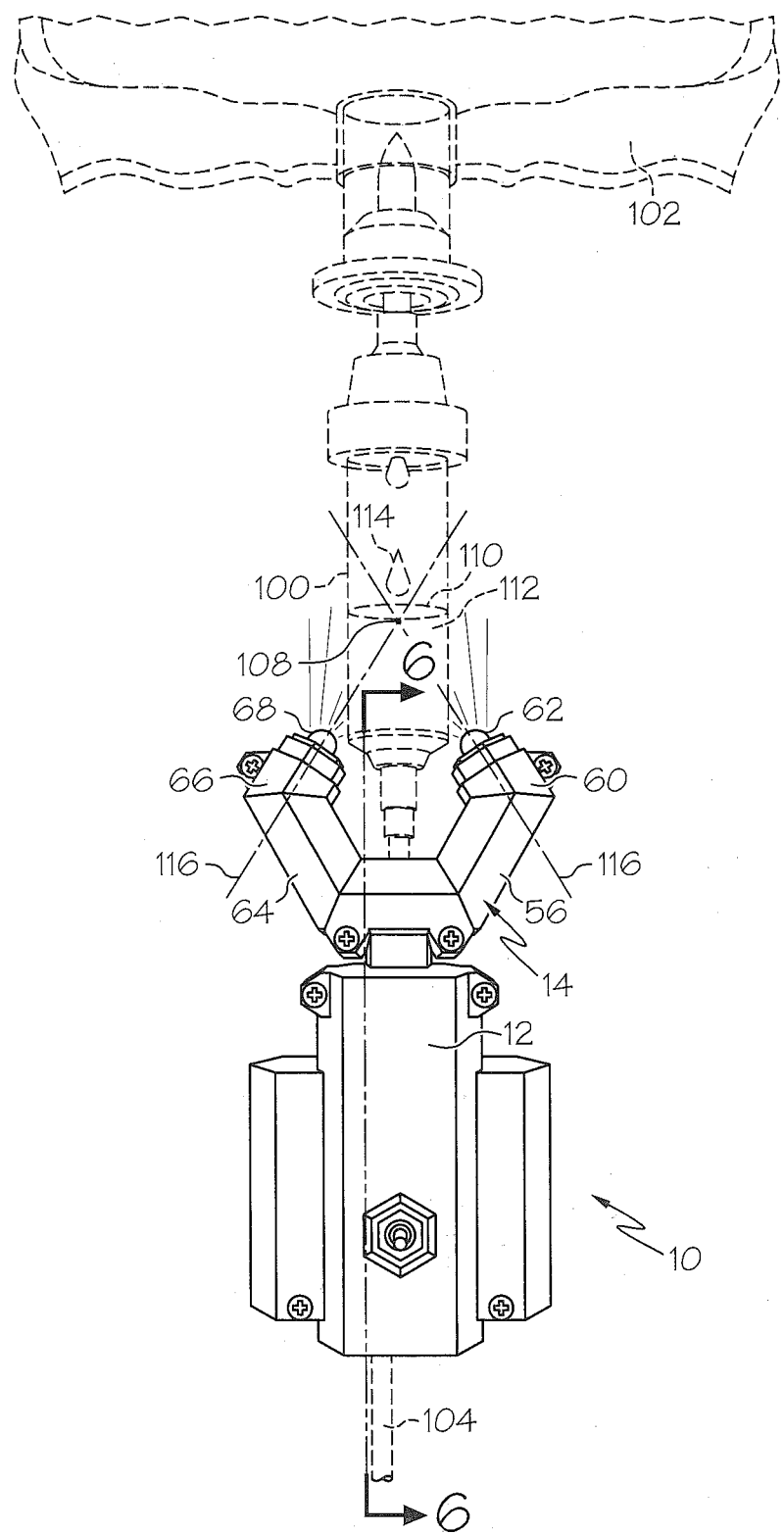
FIG. 7 is a front elevational view of the present illumination device positioned for operative use below a typical drip chamber and clipped to a typical flush line.

In use, drip chamber illumination device 10 may be used to illuminate a drip chamber 100 of a fluid feed for the medical infusion of fluids as shown in FIGS. 6 and 7. In certain medical or treatment applications, the room requires low light or darkness and the drip rate of the fluid being administered through infusion needs to be strictly monitored at least in part by observing drip chamber 100. Drip chamber 100 is inserted into and hangs from an I.V. bag 102 which contains the fluid being administered. The fluid is fed by gravity and/or external pressure into drip chamber 100. A tube/flush line 104 extends below and off of drip chamber 100 and conveys the fluid to the patient for administration.

Drip chamber illumination device 10 may be clipped onto tube/flush line 104 just below drip chamber 100 as shown in FIGS. 6 and 7. Clip 74 allows illumination device 10 to be quickly applied and removed from tube/flush line 104. As shown in FIGS. 6 and 7, drip chamber illumination device 10 is configured to be positioned below drip chamber 100. This configuration is beneficial because when the lights 62 and 68 are below drip chamber 100, illumination device 10 does not obstruct the medical personnel's view of drip chamber 100 in substantially any direction. As shown in FIG. 6, the drip chamber 100 is viewable from either side. As shown in FIG. 7, drip chamber 100 is viewable from the front or back.

As shown in FIG. 6, illumination device is clipped to tube/flush line 104. Tube/flush line 104 may be received into notch 88 of clip 74, and/or notch 90 in housing 12 or illumination arm 14, as shown. Notches 88 and/or 90 act to self-center illumination device 10 on tube/flush line 104, which effectively self-centers illumination device on drip chamber 100 as shown in FIG. 7. FIG. 6 illustrates one embodiment of illumination device 10 wherein illumination arm 14 is angularly orientated with body 12 at angle β. This angular orientation allows illumination arm 14 to be substantially vertical or aligned with drip chamber 100 when illumination device 10 is clipped to tube/flush line 104, particularly when power source 30 is housed in body housing 16 and center of mass 42 of body 12 is offset a distance $D_1$ from a connection point 106 at which first end 76 of clip 74 engages tube/flush line 104. The gravitational force effective at center of mass 42 induces a moment about connection point 106 because center of mass 42 is offset a distance $D_1$. Thus, the application of the moment results in a rotation of illumination device 10 about connection point 106. The rotation of illumination device 10 then results center of mass 42 in equilibrium substantially beneath connection point 106 and angle β results in illumination arm 14 being in a substantially vertical position or similar position wherein with light 62 (and light 68 not shown due to the section view) is directed toward meniscus 100 of drip chamber 100 as shown in FIG. 6. Angle β may be estimated or pre-determined based upon the distance $D_1$ between the center of mass 42 and connection point 106 during the design and manufacture of illumination device 10 using known methods. Accordingly, angle β may be related to or proportional the distance $D_1$ between the center of mass 42 and connection point 106.

As further shown in FIG. 7, lights 62 and 68 may be directed on a light path 116 that is ideally aimed at an acute angle to a substantially common focal point 108 within a common focal area near a meniscus 110 of a fluid reservoir 112 of drip chamber 100. Light paths 116 provided from an acute angle as shown increases the reflectivity and visibility of a stream of drops 114 and the subsequent deflection of meniscus 110 when a drop 114 penetrates meniscus 110. Moreover, light supplied from below at the acute angles shown in FIG. 6 increases the reflectivity and visibility of any bubbles that may be present within reservoir 112 of drip chamber 100.

Another benefit of having drip chamber illumination device 10 positioned below drip chamber 100 and having lights 62 and 68 directed substantially upwardly is that the light projects upward and away from the operator's eyes. This configuration minimally contaminates a darkened operating or treatment room environment, thereby preserving the medical personnel's dim-light-adjusted vision. Further, an embodiment of illumination device 10 shown in FIG. 3 allows a user to individually select the color of light for a given illumination device so that if multiple infusion lines are being used, the medical personnel may use different colors to visually differentiate each of the multiple drip chambers.

When illumination device 10 is clipped to tube/flush line 104 and lights 62 and 68 are switched on using switch 44, push-button switch 45 or dial switch (not shown), the lights illuminate drip chamber 100 and allow the medical personnel to view the drip rate of drops 114 from anywhere in the operating or treatment room. The upwardly directed light reflects off of meniscus 110 when drop 114 penetrates meniscus 110, this interruption or deflection of meniscus 110 is clearly visible.

As is evident from the foregoing description, certain aspects of the present invention are not limited to the particular details of the examples illustrated herein. It is therefore contemplated that other modifications and applications using other operator input devices and other steering gain scaling techniques will occur to those skilled in the art. It is accordingly intended that all such modifications, variations, and other uses and applications which do not depart from the spirit and scope of the present invention are deemed to be covered by the present invention.

Other aspects, objects, and advantages of the present invention can be obtained from a study of the drawings, the disclosures, and the appended claims.

I claim:
1. A drip chamber illumination device comprising:
a body having a first end and a second end;

an illumination arm having a first and a second end wherein said second end is coupled to said first end of said body;

a light source disposed proximate said first end of said illumination arm, said light source comprising at least one light, said light source being in electronic communication with a power source;

a clip operably connected to said body and configured to couple said drip chamber illumination device to a flush line;

a switch disposed on said body, said switch in electronic communication with said power source and said light source, and wherein said switch selectively provides power from said power source to selectively illuminate said light source.

2. The drip chamber illumination device of claim 1 wherein the light source comprises two lights spatially offset.

3. The drip chamber illumination device of claim 2 wherein said illumination arm comprises two aims extending outwardly off a common trunk wherein each arm includes at least one light disposed on said arm proximate a termination end of said arm.

4. The drip chamber illumination device of claim 3 wherein each of said arms further includes an inwardly extending return portion proximate said termination end and wherein said at least one light is disposed on a termination end of said return portion.

5. The drip chamber illumination device of claim 2 wherein each of said lights is directed toward a substantially common focal area.

6. The drip chamber illumination device of claim 1 wherein said light source illuminates in more than one color of light.

7. The drip chamber illumination device of claim 6 further comprising a color switch disposed on said body or on said illumination arm, said color switch configured to select the color of light dispersed by said light source.

8. The drip chamber illumination device of claim 7 wherein said color switch is a push-button switch.

9. The drip chamber illumination device of claim 1 wherein said clip is configured to self-align said drip chamber illumination device on a flush line.

10. The drip chamber illumination device of claim 9 wherein said clip has a first end and a second end and said first end includes a notch configured to receive a portion of a flush line.

11. The drip chamber illumination device of claim 10 wherein said body includes a notch configured to be complementary with said notch in said clip wherein said notch in said body and said notch in said clip are configured to receive a portion of a flush line and center said drip chamber illumination device thereon.

12. The drip chamber illumination device of claim 1 wherein said clip includes a spring that effectuates a clamping force of said clip upon said body.

13. The drip chamber illumination device of claim 12 wherein said clip is pivotally coupled to said body and said spring is a fulcrum of said clip.

14. The drip chamber illumination device of claim 13 wherein a gap is defined between said body and said clip, wherein said gap is positioned between a said first end and said fulcrum and said gap is configured for a flush line to pass therethrough.

15. The drip chamber illumination device of claim 14 wherein said clip further includes a guide wedge member configured to direct a flush line through said gap.

16. The drip chamber illumination device of claim 1 wherein said body and said illumination arm intersect at an angle.

17. The drip chamber illumination device of claim 16 wherein said clip engages a flush line at a connection point and said angle between said illumination aun and said body is proportionate to a distance between said connection point and a center of mass of said illumination device.

18. A drip chamber illumination device comprising:
a body having a first end and a second end;
an illumination arm having a first and a second end wherein said second end is coupled to said first end of said body at an angle;
a light source disposed proximate said first end of said illumination arm, said light source comprising at least two lights spatially offset wherein each of said lights has a light path and each of said light paths are aimed toward a substantially common focal area, and wherein in said light source is in electronic communication with a power source;
a clip pivotally coupled to said body and configured to removably couple said illumination device to a flush line wherein said clip engages a flush line at a connection point and said angle between said illumination aim and said body is proportionate to a distance between said connection point and a center of mass of said illumination device;
a switch disposed on said body, said switch in electronic communication with said power source and said light source, and wherein said switch selectively provides power from said power source to selectively illuminate said light source.

19. The drip chamber illumination device of claim 18 further comprising a color switch disposed on said body or on said illumination arm, wherein said light source illuminates in more than one color of light and said color switch configured to select the color illuminated by said light.

20. A drip chamber illumination device comprising:
a body having a first end and a second end;
an illumination arm having a first and a second end wherein said second end is coupled to said first end of said body;
a light source disposed proximate said first end of said illumination arm, said light source comprising at least one light, said light source being in electronic communication with a power source;
a clip operably connected to said body for coupling said drip chamber illumination device to a flush line;
a switch disposed on said body, said switch in electronic communication with said power source and said light source, and wherein said switch selectively provides power from said power source to selectively illuminate said light source; and
wherein said illumination aim comprises two arms extending outwardly off a common trunk, said trunk being proximate said second end of said illumination arm, and wherein each arm includes at least one light disposed thereon proximate a termination end of said arm.

* * * * *